United States Patent
Noel

(10) Patent No.: US 10,568,781 B2
(45) Date of Patent: *Feb. 25, 2020

(54) SANITARY NAPKINS CAPABLE OF TAKING COMPLEX THREE-DIMENSIONAL SHAPE IN USE

(71) Applicant: The Procter & Gamble Company, Cincinnati, OH (US)

(72) Inventor: John Richard Noel, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 513 days.

This patent is subject to a terminal disclaimer.

(21) Appl. No.: 15/404,770

(22) Filed: Jan. 12, 2017

(65) Prior Publication Data

US 2017/0119591 A1    May 4, 2017

Related U.S. Application Data

(63) Continuation of application No. 14/212,722, filed on Mar. 14, 2014, now Pat. No. 9,579,238, which is a
(Continued)

(51) Int. Cl.
*A61F 13/15*    (2006.01)
*A61F 13/472*    (2006.01)
(Continued)

(52) U.S. Cl.
CPC .......... *A61F 13/472* (2013.01); *A61F 13/474* (2013.01); *A61F 13/4704* (2013.01); *A61F 13/512* (2013.01); *A61F 13/51113* (2013.01); *A61F 13/51394* (2013.01); *A61F 13/53* (2013.01); *A61F 13/536* (2013.01); *A61F 13/8405* (2013.01);
(Continued)

(58) Field of Classification Search
None
See application file for complete search history.

(56) References Cited

U.S. PATENT DOCUMENTS 3,766,922 A    10/1973  Krusko
4,252,184 A     2/1981  Appel
(Continued)

FOREIGN PATENT DOCUMENTS

CN    1063815 A    8/1992
JP    58-75558     5/1983
(Continued)

OTHER PUBLICATIONS

PCT International Search Report dated Jun. 28, 2006.
http://www.engr.utk.edu/mse/Textiles/Thermal%20Bonding.htm,% 2004/2004.

*Primary Examiner* — Bradley H Philips
(74) *Attorney, Agent, or Firm* — William E. Gallagher; Andres E. Velarde

(57) ABSTRACT

A catamenial device is disclosed. The device having a topsheet, a backsheet joined to said topsheet, and an absorbent core disposed between the topsheet and the backsheet. The absorbent core has a perimeter, a longitudinal centerline, and a transverse centerline. The catamenial device further having a visible pattern having at least one circle and at least two or more slots that are visible when viewing the topsheet.

20 Claims, 6 Drawing Sheets

Related U.S. Application Data continuation of application No. 13/492,192, filed on Jun. 8, 2012, now Pat. No. 8,702,668, which is a continuation of application No. 11/059,762, filed on Feb. 17, 2005, now Pat. No. 8,211,078.

(51) Int. Cl.

| | | |
|---|---|---|
| *A61F 13/84* | (2006.01) | |
| *A61F 13/474* | (2006.01) | |
| *A61F 13/536* | (2006.01) | |
| *A61F 13/47* | (2006.01) | |
| *A61F 13/511* | (2006.01) | |
| *A61F 13/512* | (2006.01) | |
| *A61F 13/513* | (2006.01) | |
| *A61F 13/53* | (2006.01) | |

(52) U.S. Cl.
 CPC ........... *A61F 2013/51117* (2013.01); *A61F 2013/530875* (2013.01); *A61F 2013/8455* (2013.01)

(56) References Cited

U.S. PATENT DOCUMENTS

| | | |
|---|---|---|
| 4,258,704 A | 3/1981 | Hill |
| 4,326,528 A | 4/1982 | Ryan |
| 4,355,021 A | 10/1982 | Mahl |
| 4,380,450 A | 4/1983 | Reich |
| 4,394,930 A | 7/1983 | Korpman |
| 4,449,977 A | 5/1984 | Korpman |
| 4,497,435 A | 2/1985 | Trobaugh |
| 4,616,642 A | 10/1986 | Martin |
| 4,638,806 A | 1/1987 | Bartlett |
| 4,662,877 A | 5/1987 | Williams |
| 4,673,403 A | 6/1987 | Lassen |
| 4,676,871 A | 6/1987 | Cadieux |
| 4,690,679 A | 9/1987 | Mattingly, III |
| 4,690,681 A | 9/1987 | Haunschild |
| 4,740,528 A | 4/1988 | Garvey |
| 4,762,521 A | 8/1988 | Roessler |
| 4,772,282 A | 9/1988 | Oakley |
| 4,798,603 A | 1/1989 | Meyer |
| 4,837,969 A | 6/1989 | Demarest |
| 4,845,922 A | 7/1989 | Sweere |
| 4,857,044 A | 8/1989 | Lennon |
| 4,886,632 A | 12/1989 | Van Iten |
| 4,891,258 A | 1/1990 | Fahrenkrug |
| 4,892,598 A | 1/1990 | Stevens |
| 4,992,324 A | 2/1991 | Dube |
| 5,092,377 A | 3/1992 | Krumberger |
| 5,133,371 A | 7/1992 | Sivess |
| 5,135,521 A | 8/1992 | Luceri |
| 5,154,715 A | 10/1992 | Van Iten |
| 5,164,999 A | 11/1992 | Shifflett |
| 5,165,152 A | 11/1992 | Kramer |
| 5,188,625 A | 2/1993 | Van Iten |
| 5,242,435 A | 9/1993 | Murji |
| 5,293,987 A | 3/1994 | Widlund |
| 5,295,987 A | 3/1994 | Widlund et al. |
| 5,296,290 A | 3/1994 | Brassington |
| 5,300,053 A * | 4/1994 | Genaro ............ A61F 13/49007 604/378 |
| 5,316,238 A | 5/1994 | Simonson |
| 5,360,504 A | 11/1994 | Fell |
| 5,389,181 A | 2/1995 | Vukos |
| 5,396,138 A | 3/1995 | Steiner |
| 5,401,267 A | 3/1995 | Couture |
| 5,415,640 A | 5/1995 | Kirby |
| 5,437,653 A | 8/1995 | Gilman |
| 5,506,277 A | 4/1996 | Griesbach, III |
| 5,507,735 A | 4/1996 | Van Iten |
| 5,514,104 A | 5/1996 | Cole |
| 5,516,569 A | 5/1996 | Veith |
| 5,536,555 A | 7/1996 | Zelazoski |
| 5,540,827 A | 7/1996 | Deacon |
| 5,545,156 A | 8/1996 | DiPalma |
| 5,557,263 A | 9/1996 | Fisher |
| 5,560,794 A | 10/1996 | Currie |
| 5,562,649 A | 10/1996 | Chauvette |
| 5,591,147 A | 1/1997 | Couture |
| 5,599,293 A | 2/1997 | Orenga |
| 5,609,588 A | 3/1997 | DiPalma |
| 5,613,961 A | 3/1997 | DiPalma |
| 5,624,423 A | 4/1997 | Anjur |
| 5,643,240 A | 7/1997 | Jackson |
| 5,643,244 A | 7/1997 | Yamaki et al. |
| 5,659,915 A | 7/1997 | Chauvette |
| 5,667,619 A | 9/1997 | Alikhan |
| 5,667,625 A | 9/1997 | Alikhan |
| 5,674,213 A | 10/1997 | Sauer |
| 5,675,079 A | 10/1997 | Gilman |
| 5,678,206 A | 10/1997 | Ishii |
| 5,681,301 A | 10/1997 | Yang |
| 5,704,101 A | 1/1998 | Majors |
| 5,707,468 A | 1/1998 | Arnold |
| 5,713,884 A | 2/1998 | Osborn, III |
| 5,716,337 A | 2/1998 | McCabe |
| 5,722,774 A | 3/1998 | Hartz |
| 5,723,197 A | 3/1998 | Grund |
| 5,727,055 A | 3/1998 | Ivie |
| 5,785,274 A | 7/1998 | Johnson |
| 5,788,684 A | 8/1998 | Abuto |
| 5,790,036 A | 8/1998 | Fisher |
| 5,797,894 A | 8/1998 | Cadieux |
| 5,803,920 A | 9/1998 | Gilman |
| 5,816,560 A | 10/1998 | Obser |
| 5,817,394 A | 10/1998 | Alikhan |
| 5,827,256 A | 10/1998 | Balzar |
| 5,837,314 A | 11/1998 | Beaton |
| 5,853,402 A | 12/1998 | Faulks |
| 5,865,824 A | 2/1999 | Chen |
| 5,891,123 A | 4/1999 | Balzar |
| 5,910,137 A | 6/1999 | Clark |
| 5,948,829 A | 9/1999 | Wallajapet |
| 5,958,321 A | 9/1999 | Schoelling |
| 5,971,505 A | 10/1999 | Coe |
| 5,980,814 A | 11/1999 | Roller |
| 5,981,012 A | 11/1999 | Pomplun |
| 6,022,607 A | 2/2000 | James |
| 6,039,716 A | 3/2000 | Jessup |
| 6,049,916 A | 4/2000 | Rajala |
| 6,120,488 A | 9/2000 | Vanrijswijck et al. |
| 6,172,276 B1 | 1/2001 | Hetzler |
| 6,182,412 B1 | 2/2001 | Traxler |
| 6,202,717 B1 | 3/2001 | Markey |
| 6,240,569 B1 | 6/2001 | Van Gompel |
| 6,245,051 B1 | 6/2001 | Zenker |
| 6,258,427 B1 | 7/2001 | Kerins |
| 6,261,679 B1 | 7/2001 | Chen |
| 6,264,776 B1 | 7/2001 | DiPalma |
| 6,277,517 B1 | 8/2001 | Thomas |
| 6,284,261 B1 | 9/2001 | Tramontana |
| 6,298,610 B2 | 10/2001 | Traxler |
| 6,314,617 B1 | 11/2001 | Hastings |
| 6,315,765 B1 | 11/2001 | Datta |
| 6,316,687 B1 | 11/2001 | Davis |
| 6,318,555 B1 | 11/2001 | Kuske |
| 6,319,238 B1 | 11/2001 | Sartorio |
| 6,347,218 B1 | 2/2002 | Fuhrmann |
| 6,348,253 B1 | 2/2002 | Daley |
| 6,393,901 B1 | 5/2002 | Levesque |
| 6,395,956 B1 | 5/2002 | Glasgow |
| 6,395,957 B1 | 5/2002 | Chen |
| 6,409,883 B1 | 6/2002 | Makolin |
| 6,410,823 B1 | 6/2002 | Daley |
| 6,423,884 B1 | 7/2002 | Oehmen |
| 6,447,901 B1 | 9/2002 | Du |
| 6,453,628 B2 | 9/2002 | Traxler |
| 6,458,072 B1 | 10/2002 | Zunker |
| 6,465,713 B1 | 10/2002 | Gell |
| 6,479,061 B2 | 11/2002 | Fontenot |
| 6,479,728 B1 | 11/2002 | DiPalma |
| 6,481,801 B1 | 11/2002 | Schmale |

(56) References Cited

U.S. PATENT DOCUMENTS

| | | |
|---|---|---|
| 6,486,379 B1 | 11/2002 | Chen |
| 6,487,397 B2 | 11/2002 | Fuhrmann |
| 6,503,233 B1 | 1/2003 | Chen |
| 6,503,526 B1 | 1/2003 | Krzysik |
| 6,524,442 B2 | 2/2003 | Tanner |
| 6,527,757 B1 | 3/2003 | Jackson |
| 6,530,910 B1 | 3/2003 | Pomplun |
| 6,537,414 B1 | 3/2003 | Schoelling |
| 6,537,982 B1 | 3/2003 | Bishop et al. |
| H2062 H | 4/2003 | Blaney |
| 6,543,843 B1 | 4/2003 | Moilanen |
| 6,546,578 B1 | 4/2003 | Steinmeier |
| 6,562,192 B1 | 5/2003 | Hamilton |
| 6,564,942 B1 | 5/2003 | Shiffler |
| 6,566,577 B1 | 5/2003 | Addison |
| 6,582,389 B2 | 6/2003 | Buzot |
| 6,582,714 B1 | 6/2003 | Emmrich |
| 6,586,653 B2 | 7/2003 | Graeme, III |
| 6,588,080 B1 | 7/2003 | Neely |
| 6,590,138 B2 | 7/2003 | Onishi |
| 6,596,920 B2 | 7/2003 | Wehner |
| 6,600,085 B2 | 7/2003 | Sun |
| 6,600,086 B1 | 7/2003 | Mace |
| 6,601,706 B2 | 8/2003 | McManus |
| 6,603,054 B2 | 8/2003 | Chen |
| 6,607,160 B2 | 8/2003 | Lewis |
| 6,608,236 B1 | 8/2003 | Burnes |
| 6,613,955 B1 | 9/2003 | Lindsay |
| 6,617,490 B1 | 9/2003 | Chen |
| 6,620,144 B1 | 9/2003 | Glasgow |
| 6,632,205 B1 | 10/2003 | Sauer |
| 6,641,692 B2 | 11/2003 | Reynolds |
| 6,649,099 B2 | 11/2003 | Potts |
| 6,652,498 B1 | 11/2003 | Glasgow |
| 6,656,168 B2 | 12/2003 | Braverman et al. |
| 6,663,611 B2 | 12/2003 | Blaney |
| 6,667,424 B1 | 12/2003 | Hamilton |
| 6,673,982 B1 | 1/2004 | Chen |
| 6,682,512 B2 | 1/2004 | Uitenbroek |
| 6,685,932 B1 | 2/2004 | Kruchoski |
| 6,689,935 B2 | 2/2004 | Chen |
| 6,692,603 B1 | 2/2004 | Lindsay |
| 6,695,827 B2 | 2/2004 | Chen et al. |
| 6,700,034 B1 | 3/2004 | Lindsay |
| 6,706,944 B2 | 3/2004 | Qin |
| 6,708,823 B2 | 3/2004 | Cottingham |
| 6,710,477 B2 | 3/2004 | Lau |
| 6,713,159 B1 | 3/2004 | Blenke |
| 6,736,287 B2 | 5/2004 | Sauer |
| 6,740,792 B2 | 5/2004 | Waldroup |
| 6,742,646 B2 | 6/2004 | Sowden |
| 6,743,212 B1 | 6/2004 | Cole |
| 6,749,860 B2 | 6/2004 | Tyrrell |
| 6,756,520 B1 | 6/2004 | Krzysik |
| 6,759,567 B2 | 7/2004 | Colman |
| 6,761,013 B2 | 7/2004 | Tippey |
| 6,767,200 B2 | 7/2004 | Sowden |
| 6,783,019 B2 | 8/2004 | Zettle |
| 6,786,541 B2 | 9/2004 | Haupt |
| 6,787,490 B2 | 9/2004 | Shipp, Jr. |
| 6,808,801 B2 | 10/2004 | George |
| 6,822,136 B1 | 11/2004 | Niemeyer |
| 6,828,755 B1 | 12/2004 | Iverson |
| 6,837,696 B2 | 1/2005 | Sowden |
| 6,838,590 B2 | 1/2005 | Colman |
| 6,860,874 B2 | 3/2005 | Gubernick |
| 6,861,615 B2 | 3/2005 | Wojcik |
| 6,900,450 B2 | 5/2005 | Gimenez |
| 6,902,134 B2 | 6/2005 | Green |
| 6,908,458 B1 | 6/2005 | Sauer |
| 6,911,407 B2 | 6/2005 | Sherrod |
| 6,915,621 B2 | 7/2005 | Saraf |
| 6,939,914 B2 | 9/2005 | Qin |
| 6,945,967 B2 | 9/2005 | Drevik et al. |
| 6,967,178 B2 | 11/2005 | Zhou |
| 6,971,981 B2 | 12/2005 | Dobslaw |
| 6,978,123 B2 | 12/2005 | Fuhrmann |
| 6,982,094 B2 | 1/2006 | Sowden |
| 6,986,931 B2 | 1/2006 | Ackerman |
| 6,998,164 B2 | 2/2006 | Neely |
| 7,015,155 B2 | 3/2006 | Zhou |
| 7,067,711 B2 | 6/2006 | Kuroda et al. |
| 9,579,238 B2 * | 2/2017 | Noel ................ A61F 13/472 |
| 2001/0016721 A1 | 8/2001 | Salerno |
| 2002/0057792 A1 | 5/2002 | Fuhrmann |
| 2002/0124313 A1 | 9/2002 | Cook |
| 2002/0128615 A1 | 9/2002 | Tyrrell |
| 2002/0133135 A1 | 9/2002 | Gell |
| 2002/0142693 A1 | 10/2002 | Buzot |
| 2002/0147436 A1 | 10/2002 | Gell |
| 2002/0156443 A1 | 10/2002 | Drevik et al. |
| 2003/0019971 A1 | 1/2003 | Lewis |
| 2003/0023214 A1 | 1/2003 | Disalvo |
| 2003/0023217 A1 | 1/2003 | McManus |
| 2003/0047366 A1 | 3/2003 | Andrew |
| 2003/0075278 A1 | 4/2003 | Schoelling |
| 2003/0083631 A1 | 5/2003 | Chen |
| 2003/0083639 A1 | 5/2003 | Killeen et al. |
| 2003/0086973 A1 | 5/2003 | Sowden |
| 2003/0119396 A1 | 6/2003 | Koenig |
| 2003/0125682 A1 | 7/2003 | Olson |
| 2003/0125687 A1 | 7/2003 | Gubernick et al. |
| 2003/0135181 A1 | 7/2003 | Chen |
| 2003/0138097 A1 | 7/2003 | Fuhrmann |
| 2003/0143388 A1 | 7/2003 | Reeves |
| 2003/0160127 A1 | 8/2003 | Wojcik |
| 2003/0183383 A1 | 9/2003 | Strobl |
| 2003/0184136 A1 | 10/2003 | Moilanen |
| 2004/0000503 A1 | 1/2004 | Shah |
| 2004/0019339 A1 | 1/2004 | Ranganathan |
| 2004/0031121 A1 | 2/2004 | Martin |
| 2004/0054331 A1 | 3/2004 | Hamilton |
| 2004/0064117 A1 | 4/2004 | Hammons et al. |
| 2004/0074052 A1 | 4/2004 | Hlaban |
| 2004/0074053 A1 | 4/2004 | Hlaban |
| 2004/0077473 A1 | 4/2004 | Kubalek |
| 2004/0078019 A1 | 4/2004 | Elmer |
| 2004/0087924 A1 | 5/2004 | Sroda |
| 2004/0102752 A1 | 5/2004 | Chen |
| 2004/0120988 A1 | 5/2004 | Masting |
| 2004/0116014 A1 | 6/2004 | Soerens |
| 2004/0122393 A1 | 6/2004 | Morman |
| 2004/0115419 A1 | 7/2004 | Qin |
| 2004/0126543 A1 | 7/2004 | Potts |
| 2004/0127870 A1 | 7/2004 | DiPalma |
| 2004/0127873 A1 | 7/2004 | Varona |
| 2004/0223667 A1 | 11/2004 | Shah |
| 2004/0236294 A1 | 11/2004 | Drzewiecki |
| 2004/0236297 A1 | 11/2004 | Drzewiecki |
| 2004/0251292 A1 | 12/2004 | Grebonval |
| 2004/0253894 A1 | 12/2004 | Fell |
| 2004/0254549 A1 | 12/2004 | Olson |
| 2004/0259707 A1 | 12/2004 | Lochte |
| 2005/0014428 A1 | 1/2005 | Zenker |
| 2005/0022955 A1 | 2/2005 | Ward |
| 2005/0082948 A1 | 4/2005 | Li |
| 2005/0092869 A1 | 5/2005 | Vandertol |
| 2005/0096614 A1 | 5/2005 | Perez |
| 2005/0096619 A1 | 5/2005 | Costa |
| 2005/0112338 A1 | 5/2005 | Faulks |
| 2005/0113775 A1 | 5/2005 | English |
| 2005/0121347 A1 | 6/2005 | Hanson |
| 2005/0123398 A1 | 6/2005 | Tam |
| 2005/0129897 A1 | 6/2005 | Zhou |
| 2005/0130536 A1 | 6/2005 | Siebers |
| 2005/0131362 A1 | 6/2005 | Przepasniak |
| 2005/0131371 A1 | 6/2005 | Fell |
| 2005/0137557 A1 | 6/2005 | Swiecicki |
| 2005/0178788 A1 | 8/2005 | Shannon |
| 2005/0251082 A1 | 11/2005 | Del Bono |
| 2005/0256437 A1 | 11/2005 | Silcock |
| 2006/0098446 A1 | 5/2006 | Barker |

(56) References Cited

U.S. PATENT DOCUMENTS

| | | |
|---|---|---|
| 2006/0100598 A1 | 5/2006 | Tamura |
| 2015/0094681 A1 | 4/2015 | Terasoma et al. |

FOREIGN PATENT DOCUMENTS

| | | |
|---|---|---|
| JP | 59-190228 | 12/1984 |
| JP | 60-53144 | 3/1985 |
| JP | 11-226054 A | 8/1999 |
| JP | 2002-35036 A | 2/2002 |
| WO | WO 93/16670 A1 | 9/1993 |
| WO | WO 95/16424 A1 | 6/1995 |
| WO | WO 96/11107 A1 | 4/1996 |
| WO | WO 96/40513 A1 | 12/1996 |
| WO | WO 97/28773 A1 | 8/1997 |
| WO | WO 98/16262 A1 | 4/1998 |
| WO | WO 99/60912 A1 | 12/1999 |
| WO | WO 00/28929 A1 | 5/2000 |
| WO | WO 00/74476 A1 | 12/2000 |
| WO | WO 00/74740 A1 | 12/2000 |
| WO | WO 01/01909 A1 | 1/2001 |
| WO | WO 01/43849 A2 | 6/2001 |
| WO | WO 01/47459 A1 | 7/2001 |
| WO | WO 02/38097 A1 | 5/2002 |
| WO | WO 2002/091964 A1 | 11/2002 |
| WO | WO 2003/051257 A1 | 6/2003 |
| WO | WO 2003/083433 A2 | 10/2003 |
| WO | WO 2004/052414 A1 | 6/2004 |
| WO | WO 2004/080362 A1 | 9/2004 |

\* cited by examiner ically, the present invention relates to catamenial devices
SANITARY NAPKINS CAPABLE OF TAKING COMPLEX THREE-DIMENSIONAL SHAPE IN USE

FIELD OF INVENTION

This application relates to catamenial devices such as sanitary napkins for the absorption of menses. More particularly, the present invention relates to catamenial devices having a hydrophobic lotion coating on the surface of an apertured topsheet, the lotion being transferable to the wearer's skin by normal contact and wearer motion and/or body heat.

BACKGROUND OF THE INVENTION

Disposable absorbent articles, such as diapers, training pants, and catamenial devices having lotioned topsheets are known. Lotions of various types are known to provide various skin benefits, such as prevention or treatment of diaper rash. These lotions can be applied to the topsheet of absorbent articles, for example, and can be transferred to the skin of the wearer during use.

Unlike many types of disposable absorbent articles, catamenial devices such as pads and pantiliners are specifically designed to acquire menstrual fluid. Menstrual fluid differs from other exudates, such as urine, in many important properties, such as viscosity. Therefore, catamenial devices should differ in their structural components from such devices as baby diapers to be optimized for the maximum absorption of menstrual fluid.

The addition of lotion to the topsheet of absorbent articles is known to provide benefits such as easier BM clean up on babies. Likewise, lotion on topsheets is known to provide for better skin health of babies, such as the reduction of diaper rash. For example, U.S. Pat. No. 3,489,148 to Duncan et al. teaches a baby diaper comprising a hydrophobic and oleophobic topsheet wherein a portion of the topsheet is coated with a discontinuous film of oleaginous material. A major disadvantage of the diapers disclosed in the Duncan et al. reference is that the hydrophobic and oleophobic topsheets are slow in promoting transfer of urine to the underlying absorbent cores. Since the viscosity of menses is considerably greater than urine, the problems associated with Duncan et al are more profound.

One successful attempt at overcoming the problems of Duncan is disclosed in Roe et al., U.S. Pat. No. 5,968,025. Roe et al. discloses an absorbent article in which a lotion is applied to a hydrophilic topsheet (or a topsheet rendered to be hydrophilic). The hydrophilic topsheet aids in ensuring urine gushes are adequately absorbed into the underlying core, rather than running off into the sides of a baby diaper, for example.

The known attempts at applying lotions to topsheets of absorbent products have been primarily directed to baby diapers, with the benefit provided being better skin health for the bottom of the baby. Little attention has been directed to the unique problems associated with the skin of an adult woman when wearing a catamenial pad. The skin of the vulvar area of an adult woman is very different than that of a baby's bottom (or buttock skin in general), and the lotion needs are very different. For example, rather than being concerned with diaper rash, a menstruating woman is more concerned about hygiene, that is, reducing the amount of menses remaining on the skin and hair after use of a sanitary pad.

The aforementioned attempts at providing a lotion on a topsheet of an absorbent article have focused on the lotion/topsheet characteristics necessary to handle a gush of urine in a relatively short amount of time. However, for catamenial devices, the fluid insult has very different characteristics, in the context of physio-chemical properties (e.g., viscosity, fluid dynamics, etc.) and in the volume and in the time to be absorbed. For example, menstrual flow typically consists of two patterns. One of these is "trickle" flow, which varies from 0.1 to 2 ml per hour. The second pattern is "gush" flow which varies from a few ml in volume delivered over a few seconds. Gush flow can result from an accumulation of menses pooling in the vagina which can then exit the body upon a change in position, such as a transition from sitting to standing. In any event, even with gush flow, the total amount of fluid required to be absorbed into the core in a given time is much less than that required by other absorbent products, such as baby diapers, for example. One practical result is that catamenial devices, rather than needing to be designed to handle gushing fluid, more typically handle fluid through a "blotting" effect.

Accordingly, there is a continuing need for a catamenial device having improved fluid handling such that more menses enter into and remain in the device, and less on the skin and hair of the wearer.

Additionally, there is a continuing need for a catamenial device that has improved body fit to better fit the body of the wearer.

SUMMARY OF THE INVENTION

A catamenial device is disclosed. The device having a topsheet having a body facing surface, a backsheet joined to said topsheet, and an absorbent core disposed between the topsheet and the backsheet. The absorbent core has a perimeter, a longitudinal centerline, and a transverse centerline. The catamenial device further having a visible pattern having at least one circle and at least two or more slots that are visible when viewing the topsheet. The visible pattern having at least one circle and at least two or more slots share an imaginary line connecting an edge of one or more slots with an edge of one or more circles. The two or more slots are parallel to each other. The imaginary line connecting an edge of one or more slots with an edge of one or more circles forms a portion of a perimeter of the visible pattern. The slots are cut from the absorbent core, are distinct, and run substantially perpendicular to the longitudinal centerline.

A catamenial device is additionally disclosed. The device having a topsheet having a body facing surface, a backsheet joined to said topsheet, and an absorbent core disposed between the topsheet and the backsheet. The absorbent core has a perimeter, a longitudinal centerline, and a transverse centerline. The catamenial device further having a visible pattern of circles and slots within the absorbent core perimeter. The visible pattern is visible when viewing the topsheet. The visible pattern of circles and slots share an imaginary straight line connecting an edge of the slots with an edge of a plurality of circles. The slots are parallel to each other. The imaginary line connecting an edge of the slots with an edge of one or more circles forms a portion of a perimeter of the visible pattern. The slots are cut from the absorbent core, are distinct, and run substantially perpendicular to the longitudinal centerline.

A catamenial device is additionally disclosed. The catamenial device having a topsheet having a body facing surface, a backsheet joined to said topsheet, and an absorbent core disposed between said topsheet and said backsheet. The absorbent core has a perimeter, a longitudinal centerline, and a transverse centerline. The catamenial device further having a visible pattern comprising one or more circles and one or more slots within the absorbent core perimeter. The one or more slots and one or more circles share an imaginary straight line connecting an edge of the slots with an edge of one or more circles. The visible pattern and the absorbent core converge towards the longitudinal centerline. The imaginary line connecting an edge of the one or more slots with an edge of one or more circles forms a portion of a perimeter of the visible pattern. The one or more slots are cut from the absorbent core; are distinct, and run substantially perpendicular to the longitudinal centerline.

BRIEF DESCRIPTION OF THE DRAWINGS

While the specification concludes with claims particularly pointing out and distinctly claiming the subject matter of the present invention, it is believed that the invention can be more readily understood from the following description taken in connection with the accompanying drawings, in which:

DETAILED DESCRIPTION OF THE INVENTION

Figure 1:
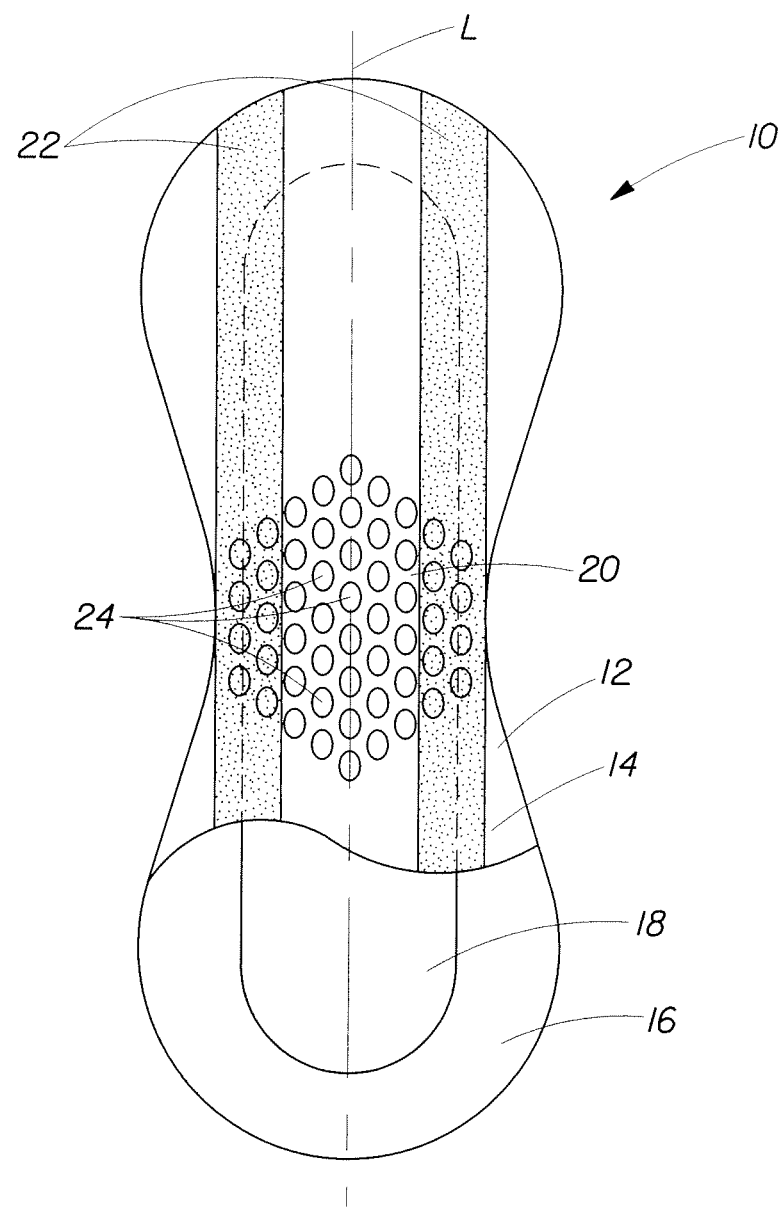
FIG. 1 is a plan view of a catamenial device having an apertured topsheet and a lotion composition.

FIG. 1 shows a catamenial device 10, that can be a sanitary napkin or pantiliner, having a body-contacting surface 12 and a topsheet 14 at least a portion 20 of which has a plurality of apertures 24. Device 10 has a liquid impervious backsheet 16 joined to the topsheet 14, and an absorbent core 18 disposed between the topsheet and backsheet. The sanitary napkin 10 has a longitudinal axis L and may also be provided with additional features commonly found in sanitary napkins, including "wings" or "flaps" (not shown) as is known in the art, and/or a fluid acquisition layer between the topsheet and the absorbent core to promote fluid transport from the topsheet to the absorbent core 18. The topsheet 14 of the catamenial device 10 of the present invention has a lotion composition 22 disposed onto at least the body-contacting surface 12 thereof.

The terms "body-contacting surface" and "wearer-contacting surface" are used interchangeably herein and refer to one or more surfaces of any article component that is intended to be worn or positioned toward or adjacent the body of the wearer/user for contact between the wearer/user and the article's surface at some time during the use period. The term "garment surface" as used herein refers to the outer or exterior surface of any article component that is intended to be worn or positioned adjacent a wearer's undergarments, or in the case of an absorbent article which is not worn by the user, the garment surface is typically positioned adjacent a user's hand or other implement assisting in the use of the absorbent article. As used herein, the term "wearer" and "user" are used interchangeably as the present invention contemplates absorbent articles which may not be intended to be worn, but rather used to absorb bodily exudates while transferring the lotion compositions of the present invention.

Figure 2:
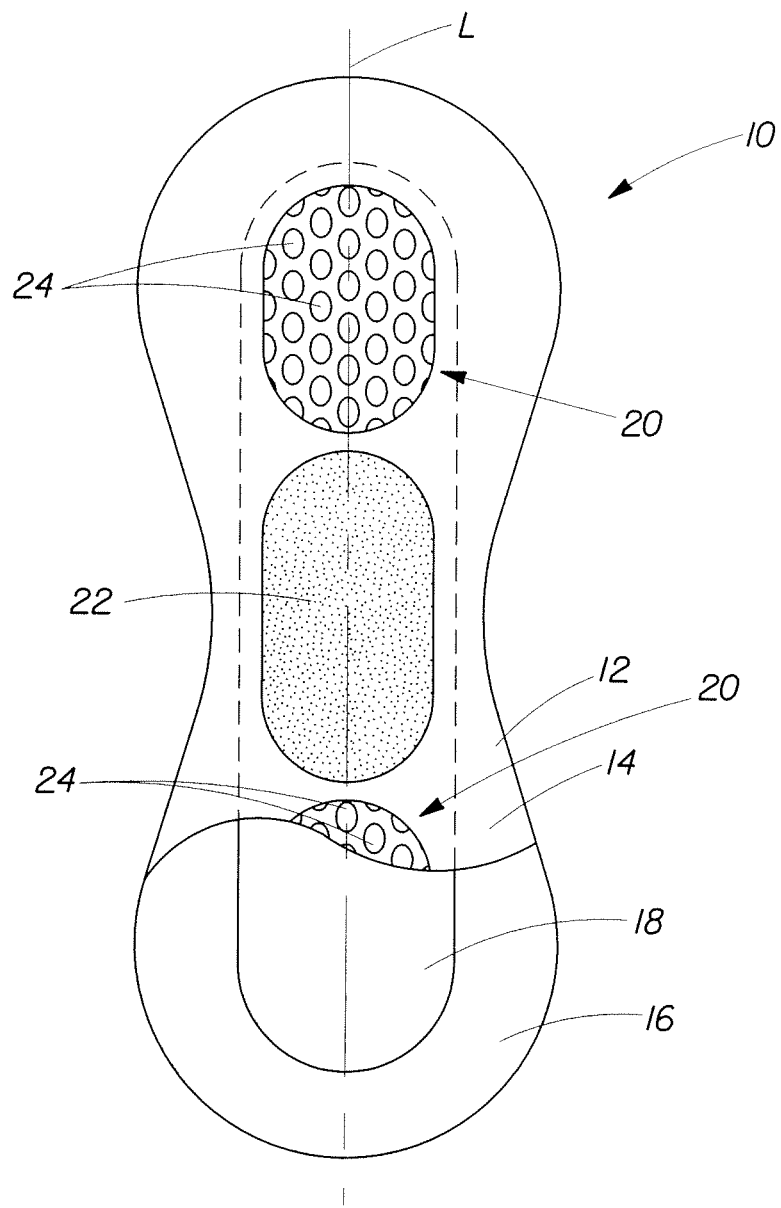
FIG. 2 is a plan view of a catamenial device having an apertured topsheet and a lotion composition.

In FIG. 1 the lotion composition (lotion) 22 is shown as applied in two parallel stripes or bands. Lotion 22 can be applied by means known in the art in any pattern known in the art. For example, lotion 22 can be applied as beads, bands, stripes, and continuous coatings. As shown in FIG. 2, lotion 22 can be applied in a discrete zone such as a centrally-disposed region of the body-contacting surface 12.

The topsheet 14 of the sanitary napkin can comprise an apertured formed film as is known in the art of sanitary napkins, including Dri-Weave® topsheets used on Always® sanitary napkins. Likewise, the topsheet 14 can be an apertured nonwoven web, for example an apertured nonwoven as disclosed in U.S. Pat. No. 5,628,097 issued May 13, 1997 to Benson et al., or U.S. Pat. No. 5,916,661 issued Jun. 29, 1999 to Benson et al. Topsheet 14 has apertures 24 therethrough on at least a portion 20 thereof to aid in fluid acquisition of viscous menstrual fluid, or sudden gushes of fluid. As shown in FIG. 1, a central portion overlying the absorbent core 18 has a plurality of apertures in a generally oval-shaped pattern. Apertures can be formed by any means known in the art, including by hydroforming (for both film and nonwoven topsheets), hot pin apertureing, slit and stretch, and the like.

The portion 20 of the topsheet 14 comprising a plurality of apertures 24 need not be limited to oval shapes or limited to being in a central portion overlying the absorbent core 18. For example, as shown in FIG. 2, the portion 20 of the topsheet 14 having a plurality of apertures can be disposed off center, nearer one end of device 10 than the other. Likewise, the plurality of apertures can form a pattern of any shape, including the substantially circular shape shown in FIG. 2.

In general the portion 20 comprising apertures 24 can be identified by the density of apertures that make up the portion 20. For example, apertures can be in relatively closely-spaced rows of closely-spaced apertures to form a region or zone of apertures as shown in FIGS. 1 and 2. Likewise, there may be more than one portion 20, i.e., more than one region or zone, of apertures 24 in topsheet 14.

In one embodiment, topsheet 14 was a 30 gsm hydrophobic bicomponent fibrous nonwoven purchased from Pegas and apertured according to the process as disclosed in U.S. Pat. No. 5,628,097 issued May 13, 1997 to Benson et al., or U.S. Pat. No. 5,916,661 issued Jun. 29, 1999 to Benson et al. Apertures 24 were on average 2.3 mm2 in area and the portion 20 comprising apertures 24 had an average percent open area of 23%. Aperture size and percent open area can be varied for each zone 20. For example, apertures can be from about 2 mm2 to about 5 mm2 and the percent open area can be from about 10% to about 50%.

Apertures 24 served the beneficial purpose of providing an open passageway for more viscous fluids or fluids having a solid particle content that do not absorb by ordinary capillarity principles. For example, menses is both relatively viscous (compared to urine or water) and contains a significant amount of solid components, as well as clumped, stringy, or otherwise difficult to absorb fluid components. Such components, as well as the less viscous components of menses can easily and quickly have access to the absorbent core of the device 10 by passing through apertures 24.

In the embodiment shown in FIG. 2 apertures 24 can serve the additional benefit of capturing fluid and fluid components that would otherwise tend to run off of the device 10 and possibly soil the garments of the wearer. For example, if fluid were to run off toward the longitudinal end of the device 10 shown in FIG. 2, the portion 16 of apertures 24 could intercept the fluid as it progressed, permitting a relatively unobstructed passage to an underlying absorbent core.

In one embodiment the topsheet can have a plurality of portions 16 in which the portions 16 differ in percent open area, and/or the plurality of apertures 24 of each respective portion 16 differ in area size. For example, a device 10 can have a central portion 16 as shown in FIG. 1 can have relatively small apertures, for example having an area of from 1 mm² to about 3 mm², and a longitudinally-displaced portion 16 as shown in FIG. 2 having relatively large apertures, for example having an area from about 2 mm² to about 5 mm². In general, in a device 10 of the present invention, the area size of apertures 24 can be varied, either randomly, or in a gradual gradient from one portion of the device to another. Area size can be varied with respect to device location by varying the length of the melt bond sites and/or amount of stretch in ring rolling when apertures are produced by the method as disclosed in U.S. Pat. No. 5,628,097 issued May 13, 1997 to Benson et al., or U.S. Pat. No. 5,916,661 issued Jun. 29, 1999 to Benson et al.

The topsheet 14 of a sanitary napkin can have various optional characteristics, as is known in the art. For example, the topsheet 14 can have channels embossed or other textured surfaces therein to direct fluid flow. Secondary topsheets, often called acquisition and/or distribution layers, can be bonded to the topsheet. Various visual signals, indicia, or other markings can be added, for example by ink jet printing.

The apertured topsheet 14 in combination with the lotion composition 22 of the present invention offer significant advantages over known topsheets and lotion combinations. The advantage can be appreciated with an understanding of the difference between menstrual fluid flow and urine flow in babies, for example. Topsheets of baby diapers are generally taught to be hydrophilic, with or without a lotion applied, such that sudden gushes of urine can be acquired through the topsheet and into the core with minimal runoff of fluid. However, it has been discovered that menstrual fluid, which has a much greater viscosity and much lower fluid flow, both in quantity and time, can be very effectively handled with a hydrophobic topsheet. Whereas urine may simply run off of a hydrophobic topsheet, particularly one that is treated with a hydrophobic lotion, it has unexpectedly been found that such a structure provides for superior benefits in a catamenial pad for menstruating women. However, the benefit observed by use of a relatively hydrophobic lotion and topsheet is much enhanced by having apertures that can better pass viscous fluid, or fluid that has relatively solid particle content, such as menses. Thus, for fluids that normally don't flow well in capillary structures anyway, the apertures, in addition to the hydrophobic nature of the lotion, aid in capturing and passing such fluid to an underlying absorbent core.

The benefit of the present invention can be optimized by tailoring the open area of the apertures 24 and the percent open area of the portion 20 with respect to the caliper (thickness) of the topsheet to be optimized for a given fluid, e.g., menses, to be absorbed into an underlying layer, such as a secondary topsheet or an absorbent core layer. It is believed that it is beneficial to use a hydrophilic absorbent core 18 and to keep the topsheet 14 in sustained intimate contact with the absorbent core 18. In this manner, there is a better likelihood that menses entering apertures 24 pass through and into the core 18, rather than being held in the apertures 24. In general, for a given fluid, topsheet and absorbent core system, it is believed beneficial to increase the percent open area with an increase in thickness (which can be an increase in basis weight). In one embodiment, a nonwoven topsheet having a relatively low caliper of about 1 mm can have a percent open area of about 20% to about 30%. A topsheet having a relatively high caliper of about 3 mm can have a percent open area of about 30% to about 50%.

An unexpected benefit of using the relatively hydrophobic lotion on the device 10 of the present invention is that coating of the skin and hair of the vulvar region during use of a the device of results in cleaner skin and hair of the vulvar region. Cleaner body benefits are further enhanced by better fluid acquisition of the fluid due to the apertures that are better at handling viscous fluids, particularly in gush events. The relatively hydrophobic topsheet 14 and lotion 22 each help prevent rewet of absorbed fluids back to the skin of the wearer. The apertures 24 help prevent run off of fluid from the pad onto the garments of the wearer. Thus, both clean body benefits and clean garment benefits can be achieved by the present invention.

In one embodiment, the apertured topsheet 14 is hydrophobic or rendered to be hydrophobic, and the lotion is also hydrophobic. The levels of hydrophobicity can be determined by standard techniques, such as measuring angles that a drop of water makes on a surface of material at equilibrium. In general, for the purposes of this invention, a material is considered hydrophobic if a drop of water exhibits an angle of about 60 degrees or greater. Fibers are considered to be hydrophobic if film sheets formed from the polymers of the fibers would exhibit contact angles with water greater than 75 degrees, and more preferably greater than about 90 degrees. Contact angles as a measure of hydrophobicity are well known in the art, and methods for measuring contact angles are equally well known. As is well known, contact angles greater than about 90 degrees are considered hydrophobic and contact angles less than 90 degrees are considered hydrophilic. As used herein, however, contact angles of 75 degrees or greater are considered hydrophobic.

The levels of hydrophobicity of the topsheet and lotion, respectively, can be equal, or the hydrophobicity of the lotion can be greater than the hydrophobicity of the topsheet. In use, the lotion can transfer from the topsheet to the skin of the wearer, which serves to make the skin and hair hydrophobic as well. In general it is desirable that the body/pad system exhibit a hydrophobicity gradient from the body skin and hair to secure storage in an absorbent core. Therefore, in general the body can be the most hydrophobic, exhibiting a contact angle with water of about 75 degrees to about 90 degrees, with topsheet, secondary topsheets, absorbent core materials exhibiting progressively less hydrophobicity.

The advantage of the present invention can be appreciated with an understanding of the difference between menstrual fluid flow and urine flow in babies, for example. Topsheets of baby diapers are generally taught to be hydrophilic, with or without a lotion applied, such that sudden gushes of urine can be acquired through the topsheet and into the core with minimal runoff of fluid. However, it has been discovered that menstrual fluid, which has a much greater viscosity and much lower fluid flow, both in quantity and time, can be very effectively handled with a hydrophobic topsheet. Whereas urine may simply run off of a hydrophobic topsheet, particularly one that is treated with a hydrophobic lotion, it has unexpectedly been found that such a structure provides for superior benefits in a catamenial pad for menstruating women. Another unexpected benefit is the coating of the skin and hair of the vulvar region during use of a catamenial device of the present invention that results in cleaner skin and hair of the vulvar region. Yet, another benefit is better fluid acquisition of the fluid due to transfer of the lotion to the skin of the wearer that minimizes fluid transport on the skin and hair of the wearer away from the point of exit.

Without being bound by theory, it is believed that the superior benefits of the present invention are best exhibited by the combination of a hydrophobic topsheet and a hydrophobic lotion. A lotion is considered hydrophobic, for example, if the hydrophilic/lipophilic balance (HLB) is less than or equal to 7.

The lotion compositions of the present invention can comprise a select combination of skin treatment agents such as hexamidine, zinc oxide, and niacinamide which are highly effective in the prevention and treatment of erythema, malodor, and bacterial skin disorders, especially when these lotion compositions are administered to the skin from application on absorbent articles.

The benefit of using the lotions described herein can be enhanced by having a device 10 that exhibits better fit with the body of the wearer. Better fit can be achieved by incorporating folding and bending features, as well as decoupling features such as those disclosed in co-pending, commonly assigned U.S. Ser. No. 10/613,296, filed Jul. 3, 2003 in the name of Lavash. It is believed that having an absorbent core that can fold, bend, or otherwise conform to a preferred shape that better fits the body. Better fit is particularly important for devices 10 having an overall thickness of less than about 10 mm or less than about 5 mm, such as sanitary napkins marketed as "ultra" such as Always® Ultra sanitary napkins. One such sanitary napkin is described in U.S. Pat. No. 4,950,264, issued to Osborn on Aug. 21, 1990. Osborn '264 (the disclosure of which is incorporated by reference herein below) describes a thin and flexible sanitary napkin for wearing adjacent to the pudendal region (i.e., the externally visible female genitalia) and having a caliper of about 4.0 mm to about 5.0 mm, but preferably less than about 3.0 mm, or less than about 2.6 mm, or less than about 2.2 mm, or less than about 2.0 mm. In one embodiment, the caliper is 1.9 mm Osborn discloses a method of measuring caliper which includes the use of a comparator gauge, using a circular foot made of aluminium and having a weight of 10.0 grams and a contact surface of 5.16 square cm. Osborn discloses Other suitable methods describing a process for treating the topsheet with a surfactant are disclosed in U.S. Pat. Nos. 4,988,344 and 4,988,345, both issued to Reising et al. on Jan. 29, 1991. The topsheet can comprise hydrophilic fibers, hydrophobic fibers, or combinations thereof.

Figure 3:
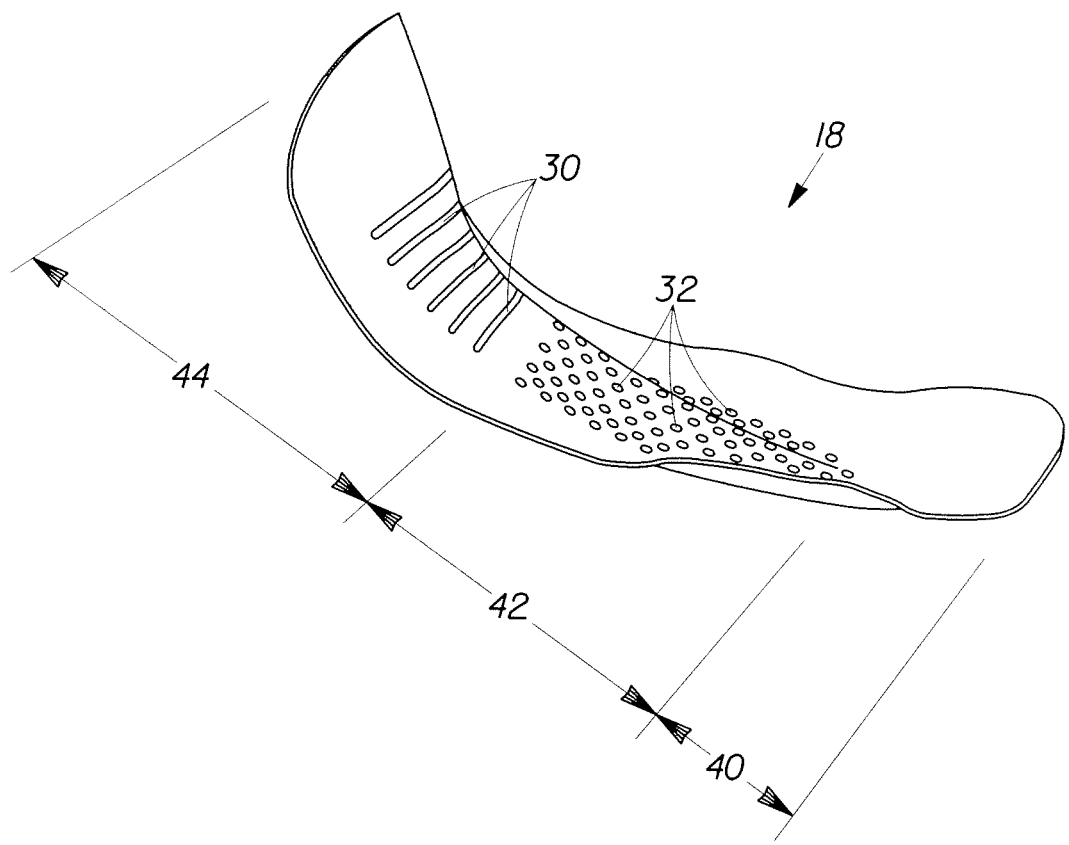
FIG. 3 is a perspective view of an absorbent core of the present invention in an in-use configuration.

Desirable fit of a device 10 used as a sanitary napkin can be described as having the shape shown in FIG. 3. That is, in use the device 10 can be cup-shaped in the front, "W" shaped in the middle, and "V" shaped in the back, as well as being generally concave from front to back. This complex shape is difficult to achieve when making and marketing devices such as sanitary napkins in generally flat or flat folded configurations.

Because many elements of a device 10, such as topsheets or backsheets, are inherently flexible and pliable, improved fit can be best facilitated by providing an absorbent core that is adapted to permit conformable fit when the product is in use. Such an absorbent core can have the features shown in FIG. 4.

An absorbent core can have discrete zones of varying flexibility that act as shaping elements. The zones can be defined by varying patterns of material modification. One material useful for such a core is a soft, absorbent foam, such as polyurethane foam or HIPE foam. In one embodiment, device 10 comprises a high capacity and highly absorbent core 18. Absorbent core 18 can be an airlaid core of the type disclosed in U.S. Pat. No. 5,445,777; or U.S. Pat. No. 5,607,414. Absorbent core 18 can be the type generally referred to as HIPE foams, such as those disclosed in U.S. Pat. Nos. 5,550,167; 5,387,207; 5,352,711; and 5,331,015. In a preferred embodiment, absorbent core 18 has a capacity after desorption at 30 cm of less than about 10% of its free absorbent capacity; a capillary absorption pressure of from about 3 to about 20 cm; a capillary desorption pressure of from about 8 to about 25 cm; a resistance to compression deflection of from about 5 to about 85% when measured under a confining pressure of 0.74 psi; and a free absorbent capacity of from about 4 to 125 grams/gram. Each of these parameters can be determined as set forth in U.S. Pat. No. 5,550,167. issued Aug. 27, 1996 to DesMarais. One advantage of utilizing the airlaid or HIPE foam cores as disclosed is that the absorbent core can be made very thin. For example, an absorbent core of the present invention can have an average caliper (thickness) of less than about 3 mm, or less than about 2 mm, and the thickness can be less than about 1 mm Foams can be more easily modified than conventional absorbent core materials, such as nonwoven batts, airfelt, and coform materials. However, forming apertures or slots as disclosed below can be achieved in foams more easily with known die cutting equipment, including rotary die cutters as disclosed in U.S. Pat. No. 6,702,917, issued Mar. 9, 2004 to Venturino. Such rotary die cutters can be modified to cut slots 30 and cut the absorbent core to shape at the same time.

Figure 4:
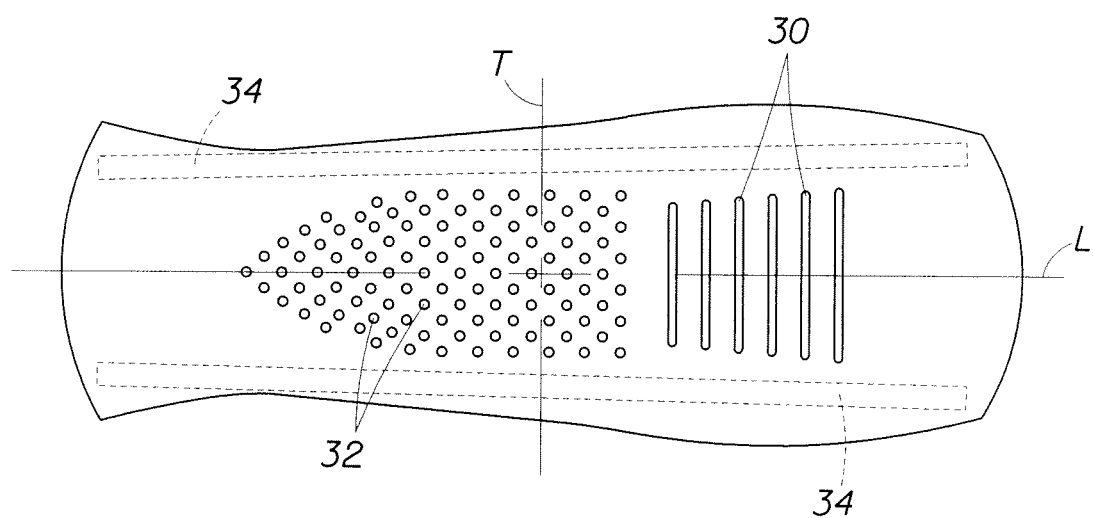
FIGS. 4-6 are plan views showing features of an absorbent core of the present invention.

As shown in FIG. 4, the absorbent core 18 can be asymmetric about a transverse centerline T, and can have a shaping element being a lateral stiffener 34. Lateral stiffener 34 can increase stiffness along the longitudinal edges of absorbent core 18. Lateral stiffener 34 can be a band or strip from about 10 mm to about 25 mm wide, and generally extend the length of the core 18. By locating the lateral stiffener 34 at the edges of the core 18 it is located in an area that undergoes little width-wise deformation when device 10 is worn, and can transfer compressive forces applied by the legs to other areas of the device where cupping or bending is desired. Lateral stiffeners 34 can comprise adhesive applied to the absorbent core or additional relative stiff materials joined to the absorbent core. If adhesive is used for lateral stiffener 34, the adhesive can also adhere the absorbent core 18 to backsheet 16.

The absorbent core 18 can have a plurality of laterally-oriented slots 30 having an average gap width of at least about 1 mm prior to use. Slots 30 are considered laterally oriented if they have a major vector component at the longitudinal centerline L that is perpendicular to the longitudinal centerline. Thus, as shown in FIG. 4, slots 30 can be substantially parallel, generally linear slots that are each parallel to centerline L, and, therefore, have no vector component in the longitudinal direction. However, slots 30 can have other configurations, including generally curved orientations such as those shown in FIGS. 5 and 6. Absorbent core can have additional modifications and features to facilitate desired bending and folding. For example, absorbent core 18 can have additional slits, apertures, perforations, lines of weakness, and the like. In particular, in one embodiment a line of weakness such as perforations or a score line along at least a portion of the longitudinal centerline L can aid in proper formation of a raised hump or ridge along the centerline.

Slots can be completely surrounded by core material. That is, slots can be entirely interiorly disposed, each slot having two ends, such as ends 31 shown in FIG. 6. In general, an imaginary straight line shown as line 33 can connect the ends 31 of slots 30 and align with an edge formed by apertures 32 in a middle zone 42 of core 18. Imaginary line 33 can correlate with an edge of lateral stiffeners 34 so as to aid in lateral compressive formation of a complex three-dimensional shape, as disclosed more fully below.

Figure 5:
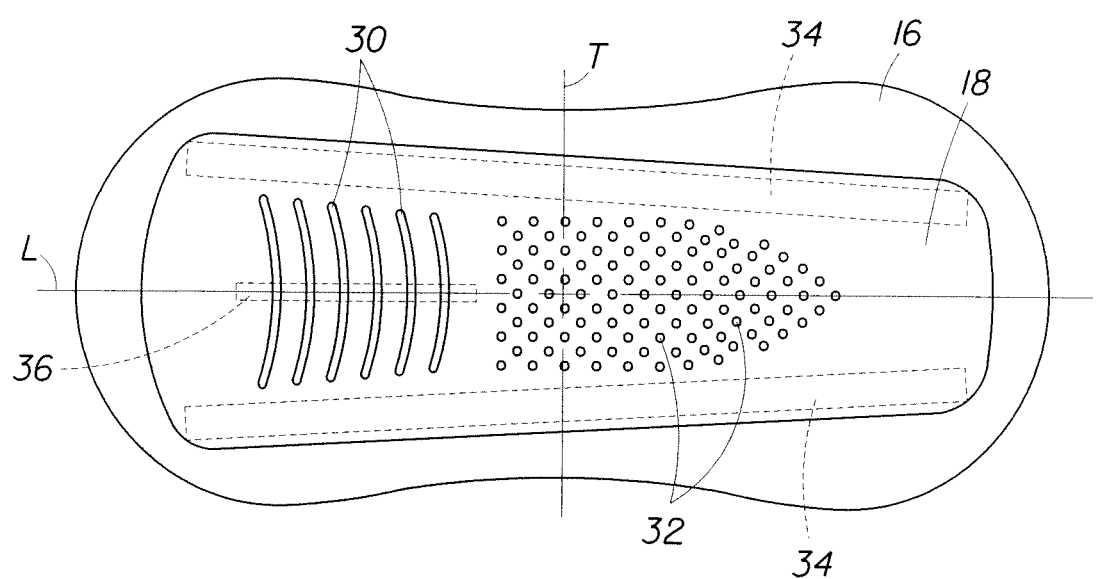
Figure 6:
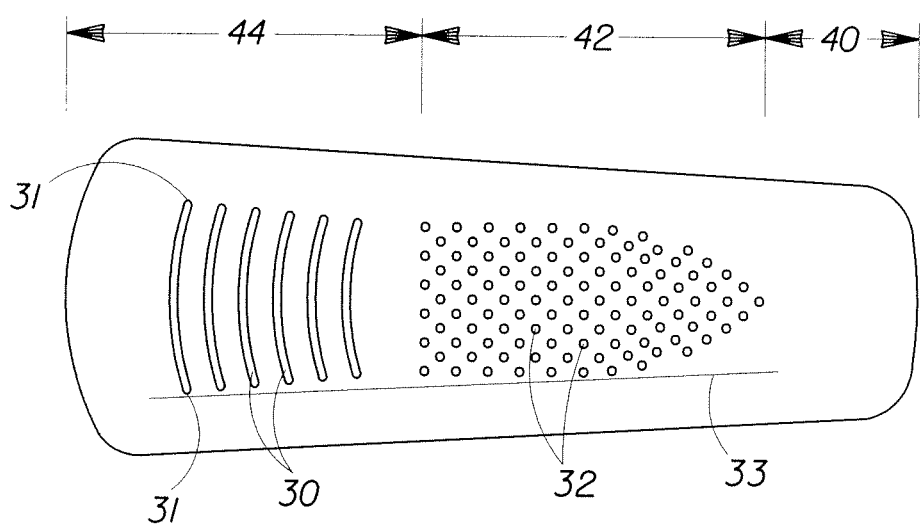

FIG. 5, which shows a sanitary napkin having the topsheet removed so as to see the absorbent core 18 positioned over backsheet 16 of a sanitary napkin having a generally hourglass shape. FIG. 6 shows the absorbent core alone and shows the three zones of the absorbent core can be identified. A first zone 40 at the front of the core 18, which is the narrowest end of an asymmetric core can have only the lateral stiffeners and cup into a concave form when worn. A middle zone 42 can comprise apertures 32 that can both help fluid acquisition as well as reduce stiffness in the middle zone. Stiffness can be reduced as required or desired by making more or fewer apertures, or by varying the size and area density of the apertures 32. A third zone 42 at the rear of the core 18, which is intended to be the back of the device 10 when worn, can have the slots 30.

Slots 30 provide for a reduction in bending resistance when the device 10 is bent as shown in FIG. 3. That is, when the device is worn, and the rear portion including the third zone of the core 18 is bent about the wearer's buttocks, including the gluteal groove, device 10 can bend accordingly due to the slots 30 which allow compression of the core in this area. Thus, as device 10 bends in a concave form about the wearers anatomy, absorbent core 10 can bend and conform accordingly due to the lack of material where material has been removed for slots 30, permitting compression about that area.

Compression of slots 30 in bending accomplishes both ease of bending about the wearer's anatomy for better fit and comfort, and ease of bending into a substantially inverted "V" shape to fit into the gluteal groove of the wearer, thereby minimizing fluid runoff from the body in this region. Therefore, both longitudinal folding is accomplished in multiple axes, aiding in both fit and fluid handling advantages. It has been found that slots spaced so as to provide compression along about 12 mm of the longitudinal axis in the rear portion of the device 10 can be sufficient for the fit and fluid protection benefit. In one embodiment, 6 slots spaced about 10 mm apart and having a width of about 2 mm was found sufficient.

The absorbent core 18 of the present invention permits the device 10 to be produced as a two-dimensional, flat device for packaging, and yet to achieve a complex three dimensional shape when used by the wearer. To aid in taking the complex three dimensional shape, absorbent core 18 can have added to it an elastic member 36. Elastic member 36 can be a strand of elastic material that is attached or joined to core 18 at least at two ends thereof. Elastic member 36 can provide for 15 mm to 50 mm of contraction with a contractive force of about 40 grams to about 100 grams. In one embodiment, elastic member can provide for 20 mm to 30 mm of contraction, and the contractive force can be 50 grams to 60 grams. Elastic member can be Stretchrite® soft stretch elastic 3 mm wide (about 0.125 inch) available from Rhode Island Textile Co. of Pawtucket R.I. When packaged in a general flat condition, elastic 36 can be in a stretched position. Upon removing from the package and/or when worn, elastic 36 can contract, causing the third zone to compress in the region of slots 30. The contraction of an elastic strip or strand 36 aligned along longitudinal centerline L, as shown in FIG. 5, tends to draw the absorbent core into a more defined and stable inverted V-shape in the rear portion of device 10.

The term "skin treatment agent" as used herein refers to materials that when applied topically and internally to the skin are capable of preventing, reducing, and/or eliminating any occurrence of skin disorders, particularly skin disorders associated with erythema, malodor, and bacterial infections. The term "skin disorders" as used herein refers to symptoms associated with irritating, acute, or chronic skin abnormalities. Examples of such symptoms include, but are not limited to, itching, inflammation, rash, burning, stinging, redness, swelling, sensitivity, sensation of heat, flaking/scaling, malodor, and the like. The term "ambient conditions" as used herein refers to surrounding conditions at about one atmosphere of pressure, at about 50% relative humidity, and at about 25° C.

The lotion compositions of the present invention can comprise, consist of, or consist essentially of the elements and limitations of the invention described herein, as well as any of the additional or optional ingredients, components, or limitations described herein. All percentages, parts and ratios are by weight of the total composition, unless otherwise specified. All such weights as they pertain to listed ingredients are based on the specific ingredient level and, therefore, do not include carriers or by-products that may be included in commercially available materials, unless otherwise specified.

The lotion compositions of the present invention comprise relatively low concentrations of a select combination of skin treatment agents that are capable of reducing and eliminating the occurrence of skin disorders that can result from contact between the skin and moisture-laden air, skin disorders resulting from prolonged moist human tissue that can occur from the skin being exposed to moisture or other body exudates, and/or skin disorders that are generated from contact between the skin and microbial or bacterial agents. The phrase "select combination of skin treatment agents" refers to the following combinations: a. hexamidine, zinc oxide, and niacinamide; b. hexamadine and zinc oxide; and c. hexamadine and niacinamide.

Surprisingly, the select combination of skin treatment agents can be included at low individual concentrations, relative to their use in the prior art, and still be effective. For example, the lotion compositions of the present invention can include hexamidine at a concentration of about 0.1% or less by weight, zinc oxide at a concentration of about 1% or less by weight, and niacinamide at a concentration of about 2% or less by weight to achieve equal or superior benefits in the prevention and/or treatment of skin disorders as compared to known lotion compositions that generally comprise these skin treatment agents at higher levels. Similarly, the total effective concentration of the select combination of skin treatment agents in the compositions of the present invention are also relatively low. The total concentration of the select combination of skin treatment agents ranges from about 0.002% to about 10%, preferably from about 0.01% to about 5%, more preferably from about 0.1% to about 2% by weight of the lotion composition.

The lotion compositions of the present invention comprise hexamidine skin treatment agent at concentrations ranging from about 0.001% to about 0.1%, from about 0.005% to about 0.1%, or even from about 0.01% to about 0.1% by weight of the composition. The hexamidine skin treatment agent suitable for use herein include those aromatic diamines which generally conform to the following formula:

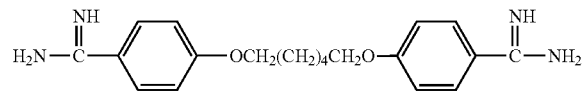

These aromatic diamines are referred to as 4,4'-[1,6-Hexanediylbis(oxy)]bisbenzenecarboximidamide; 4,4'-(hexamethylenedioxy)dibenzamidine; and 4,4'-diamidino-α,ω-diphenoxyhexane. The most popular employed form of hexamidine is the general category of hexamidine salts, which include acetate, salicylate, lactate, gluconate, tartarate, citrate, phosphate, borate, nitrate, sulfate, and hydrochloride salts of hexamidine. Specific nonlimiting examples of hexamidine salts include hexamidine isethionate, hexamidine diisethionate, hexamidine hydrochloride, hexamidine gluconate, and mixtures thereof. Hexamidine isethionate and hexamidine diisethionate are β-hydroxyethane sulfonate salts of hexamidine which are preferred for use herein as a skin treatment agent in the prevention and/or treatment of skin disorders. Hexamidine diisethionate is the most preferred hexamidine compound suitable for use as the skin treatment agent herein and is available from Laboratories Serolobilogiques (Pulnoy, France) and the Cognis Incorporation (Cincinnati, Ohio) under the tradename ELASTAB HP100.

Hexamidine compounds are known as effective skin treatment agents that can control microbial growth that can lead to irritating and itching skin disorders. Therefore, these skin treatment agents are often referred to as antimicrobial agents. As used herein the term "antimicrobial agents" refer to materials which function to destroy or suppress the growth or metabolism of microbes, and include the general classification of antibacterial, antifungal, antiprotozoal, antiparasitic, and antiviral agents.

It has been found, however, that a low concentration (about 0.1% or less by weight) of hexamidine provides for improved reduction and/or prevention of skin irritating infections, especially when a low amount of hexamidine is combined with a low concentration of other antimicrobial agents such as zinc oxide and/or niacinamide. This combination of hexamidine and zinc oxide and/or niacinamide can be administered topically and internally at a total concentration less than an effective amount of an applied dosage of these individual compounds. As used herein the term "effective amount" refers to an amount with provides a therapeutic benefit with minimal or no adverse reaction in the reduction and/or prevention of any noticeable or unacceptable skin abnormality which causes irritating, acute, or chronic symptoms including itching and inflammation.

Other aromatic diamines are also suitable for use as a skin treatment agent herein. Such compounds include butamidine and derivatives thereof including butamidine isethionate; pentamidine and derivatives thereof including pentamidine isethionate and pentamidine hydrochloride; dibromopropamidine and derivatives thereof including dibromopropamidine isethionate; stilbamidine and derivatives thereof including hydroxystilbamidine, stilbamidine dihydrochloride, and stilbamidine isethionate; diaminodiamidines and derivatives thereof; and mixtures thereof.

B. Zinc Oxide:

The lotion compositions of the present invention comprise zinc oxide skin treatment agent at concentrations ranging from about 0.001% to about 10%, preferably from about 0.005% to about 5%, more preferably from about 0.005% to about 2%, most preferably from about 0.01% to about 1% by weight of the composition. The zinc oxide skin treatment agent can be included in the compositions as an individual zinc oxide compound or a combination of zinc oxides, provided that the individual or combined zinc oxide can readily combine with the hexamidine and niacinamide skin treatment agents to provide antimicrobial benefits.

The zinc oxide skin treatment agent suitable for use herein include those inorganic white and yellowish-white powders that conform to the formula ZnO, and that are more fully described in *The Merck Index*, Eleventh Edition, entry 10050, p. 1599 (1989). Some particularly useful forms of zinc oxide include those that are manufactured and commercially available in average particle size diameters that range from about 1 nm (nanometer) to about 10 μm (micrometer), alternatively from about 10 nm to about 1 μm or even from about 20 nm to about 500 nm. Surprisingly, the inventors have discovered that the use of the above mentioned, relatively small nanoparticle diameter size zinc oxide avoids undesirable skin or hair whitening that results from the transfer of the zinc oxide containing emollient from the topsheet of absorbent article to the wearer's body during product use. This is a particular benefit when the product is a panty liner, sanitary napkin, incontinence brief, or other absorbent article intended to be used by adults having hair in the region where the lotion composition will transfer.

Commercially available zinc oxides include the white zinc oxide powders sold under the tradename ULTRAFINE 350 which is commercially available from the Kobo Incorporation located in South Plainfield, N.J. Other suitable zinc oxide materials include a premix of zinc oxide and a dispersing agent such as polyhydroxystearic acid wherein this premix is available from the Uniqema Incorporation (Wilimington, Del.) under the tradename Arlecel® P100; and a premix of zinc oxide and an isononyl isononanoate dispersing agent which is available from the Ikeda Incorporation (Island Park, N.Y.) under the tradename Salacos® 99.

The lotion compositions of the present invention comprise niacinamide skin treatment agent as an individual niacinamide or as a combination of niacinamides at a total niacinamide concentration ranging from about 0.01% to about 10%, preferably from about 0.05% to about 5%, more preferably from about 0.2% to about 2% by weight of the lotion composition. The niacinamide skin treatment agent provides for skin conditioning benefits as well as providing for increased efficacy of the skin treatment agents in controlling skin disorders.

Nonlimiting examples of niacinamide skin treatment agents suitable for use in the lotion compositions of the present invention include those niacinamide compounds that are amide derivatives of nicotinic acid, and that generally conform to the following formula:

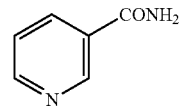

Niacinamide and nicotinic acid are also known as Vitamin $B_3$ and Vitamin $B_5$, whereas niacinamide is the commonly used active form. Niacinamide derivatives including salt derivatives are also suitable for use herein as a skin treatment agent. Nonlimiting specific examples of suitable niacinamide derivatives include nicotinuric acid and nicotinyl hydroxamic acid.

The niacinamide skin treatment agent can also be included in the composition as acidified niacinamide compounds. The process of acidifying niacinamide compounds is within the gambit of those skilled in the art, wherein one such technique involves dissolving niacinamide in an alcohol solution, adding while stirring an equal molar amount of a fatty acid such as stearic acid (e.g., mixing 1 part niacinamide to 2.4 parts stearic acid), and then air drying the mixture until the alcohol evaporates. A suitable stearic acid compound that can be used in the process of acidifying niacinamide is stearic acid sold under the tradename Emersol® 150 which is available from the Cognis Corporation.

Examples of the above niacinamide compounds are well known in the art and are commercially available from a number of sources, for example, the Sigma Chemical Company (St Louis, Mo.); ICN Biomedicals, Incorporation (Irvin, Calif.); Aldrich Chemical Company (Milwaukee, Wis.); and Em Industries HHN (Hawthorne, N.Y.).

Nonlimiting examples of optional suitable skin treatment actives useful in the present invention include allantoin; aluminum hydroxide gel; calamine; cysteine hydrochloride; racemic methionine; sodium bicarbonate; Vitamin C and derivatives thereof; protease inhibitors including serine proteases, metalloproteases, cysteine proteases, aspartyl proteases, peptidases, and phenylsulfonyl fluorides; lipases; esterases including diesterases; ureases; amylases; elastases; nucleases; guanidinobenzoic acid and its salts and derivatives; herbal extracts including chamomile; and mixtures thereof. Guanidinobenzoic acid and its salts and derivatives are more fully described in U.S. Pat. No. 5,376,655, issued to Imaki et al. on Dec. 27, 1994. These other suitable skin treatment actives are typically included at concentrations ranging from about 0.001% to about 10% by weight of the lotion composition.

Where included, panthenol typically comprises from about 0.001% to about 10%, preferably from about 0.005% to about 5%, more preferably from about 0.05% to about 1% by weight of the lotion composition. The optional panthenol skin conditioning agent provides for skin emolliency benefits that can leave the skin feeling smooth, soothing, and soft during and after interaction of the skin tissues with the skin treatment agents. The lotion compositions of the present invention can include an individual panthenol compound or a mixture of panthenol compounds.

Where included, the lotion compositions comprise the preferred optional glycerine skin conditioning agent at concentrations ranging from about 0.01% to about 10%, preferably from about 0.02% to about 5%, more preferably from about 0.05% to about 2% by weight of the lotion composition. The optional glycerine skin conditioning agent also provides for skin emolliency benefits such as smooth, soothing, and soft feeling skin, as well as being a dispersing agent for the niacinamide skin treatment agent.

The lotion compositions comprise the preferred optional chamomile oil at concentrations ranging from about 0.0001% to about 10%, preferably from about 0.001% to about 5%, more preferably from about 0.005% to about 2% by weight of the lotion composition. The optional chamomile oil skin conditioning agent also provides for skin benefits such as soothing Chamomile oil is commonly prepared as an oil extract of chamomile flowers. An example of a commercially available chamomile oil include Phytoconcentrol Chamomile which is available from Dragoco Incorporation (Totowa, N.J.).

The lotion compositions of the present invention comprise a carrier for the skin treatment agents. The carrier can be included in the compositions as an individual carrier or a combination of carrier ingredients, provided that the total carrier concentration is sufficient to provide transfer and/or migration of the skin treatment agents onto the skin. The carrier can be a liquid, solid, or semisolid carrier material, or a combination of these materials, provided that the resultant carrier forms a homogenous mixture or solution at selected processing temperatures for the resultant carrier system and at processing temperatures for combining the carrier with the skin treatment agents in formulating the lotion compositions herein. Processing temperatures for the carrier system typically range from about 60° C. to about 90° C., more typically from about 70° C. to about 85° C., even more typically from about 70° C. to about 80° C.

The lotion compositions of the present invention typically comprise the carrier at a total carrier concentration ranging from about 60% to about 99.9%, preferably from about 70% to about 98%, more preferably from about 80% to about 97% by weight of the lotion composition. Suitable carrier compounds include petroleum-based hydrocarbons having from about 4 to about 32 carbon atoms, fatty alcohols having from about 12 to about 24 carbon atoms, polysiloxane compounds, fatty acid esters, alkyl ethoxylates, lower alcohols having from about 1 to about 6 carbon atoms, low molecular weight glycols and polyols, fatty alcohol ethers having from about 12 to about 28 carbon atoms in their fatty chain, lanolin and its derivatives, glyceride and its derivatives including acetoglycerides and ethoxylated glycerides of C12-C28 fatty acids, and mixtures thereof. Alternatively or in combination with, the carrier may also be composed of polysiloxane compounds non-limiting examples include dimethicones (1-100,000,000 centistoke), cyclomethicones, alkylated silicones (hair conditioning agents), silicone gums, silicone gels, silicone waxes, copolymers of silicone (vinyl dimethicone polymers, phenyl vinyl dimethicone polymers, alkylated silicone polymers, polyethylene oxide/silicone copolymers, polyethylene oxide/alkyl silicone copolymers), and mixtures thereof.

Nonlimiting examples of suitable petroleum-based hydrocarbons having from about 4 to about 32 carbon atoms include mineral oil, petrolatum, isoparaffins, various other branched chained hydrocarbons, and combinations thereof. Mineral oil is also known as "liquid petrolatum", and usually refers to less viscous mixtures of hydrocarbons having from about 16 to about 20 carbon atoms. Petrolatum is also known as "mineral wax", "petroleum jelly", and "mineral jelly", and usually refers to more viscous mixtures of hydrocarbons having from about 16 to about 32 carbon atoms. An example of commercially available petrolatum include petrolatum sold as Protopet® 1S which is available from the Witco Corporation located in Greenwich, Conn.

Nonlimiting examples of suitable fatty alcohols having from about 12 to about 24 carbon atoms include saturated, unsubstituted, monohydric alcohols or combinations thereof, which have a melting point less than about 110° C., preferably from about 45° C. to about 110° C. Specific examples of fatty alcohol carriers for use in the lotion compositions of the present invention include, but are not limited to, cetyl alcohol, stearyl alcohol, cetearyl alcohol, behenyl alcohol, arachidyl alcohol, lignocaryl alcohol, and combinations thereof. Examples of commercially available cetearyl alcohol is Stenol 1822 and behenyl alcohol is Lanette 22, both of which are available from the Cognis Corporation located in Cincinnati, Ohio.

Nonlimiting examples of suitable fatty acid esters include those fatty acid esters derived from a mixture of $C_{12}$-$C_{28}$ fatty acids and short chain ($C_1$-$C_8$, preferably $C_1$-$C_3$) monohydric alcohols preferably from a mixture of $C_{16}$-$C_{24}$ saturated fatty acids and short chain ($C_1$-$C_8$, preferably $C_1$-$C_3$) monohydric alcohols. Representative examples of such esters include methyl palmitate, methyl stearate, isopropyl laurate, isopropyl myristate, isopropyl palmitate, ethylhexyl palmitate, and mixtures thereof. Suitable fatty acid esters can also be derived from esters of longer chain fatty alcohols ($C_{12}$-$C_{28}$, preferably $C_{12}$-$C_{16}$) and shorter chain fatty acids such as lactic acid, specific examples of which include lauryl lactate and cetyl lactate.

Nonlimiting examples of suitable alkyl ethoxylates include $C_{12}$-$C_{22}$ fatty alcohol ethoxylates having an average degree of ethoxylation of from about 2 to about 30. Nonlimiting examples of suitable lower alcohols having from about 1 to about 6 carbon atoms include ethanol, isopropanol, butanediol, 1,2,4-butanetriol, 1,2 hexanediol, ether propanol, and mixtures thereof. Nonlimiting examples of suitable low molecular weight glycols and polyols include ethylene glycol, polyethylene glycol (e.g., Molecular Weight 200-600 g/mole), butylene glycol, propylene glycol, polypropylene glycol (e.g., Molecular Weight 425-2025 g/mole), and mixtures thereof. A more detailed description of carrier ingredients including suitable hydrocarbons, polysiloxane compounds, and fatty alcohol ethoxylates can be found in U.S. Pat. No. 5,643,588, issued Jul. 1, 1997 to Roe et al. entitled "Diaper Having A Lotioned Topsheet".

In one embodiment, the carrier comprises a combination of one or more petroleum-based hydrocarbons and one or more fatty alcohols described hereinabove. When one or more petroleum-based hydrocarbons having from about 4 to about 32 carbon atoms are used in combination with one or more fatty alcohols having from about 12 to about 22 carbon atoms, the petroleum-based hydrocarbons are included at total concentrations ranging from about 20% to about 99%, preferably from about 30% to about 85%, more preferably from about 40% to about 80% by weight of the lotion composition; wherein the fatty alcohols are included at total concentrations ranging from about 0.2% to about 65%, preferably from about 1% to about 50%, more preferably from about 2% to about 40% by weight of the lotion composition.

It is believed that a petroleum-based carrier system comprising $C_4$-$C_{32}$ hydrocarbons, $C_{12}$-$C_{22}$ fatty alcohols, and fumed silica provides a homogeneous mixture of the carrier, skin treatment agents, and any optional ingredients wherein this homogeneous mixture ensures sufficient contact between the skin and skin treatment agents to result in effective prevention and treatment of skin disorders. The fumed silica suitable for inclusion in the preferred petroleum-based carrier system, or with any other carrier described herein, includes colloidal pyrogenic silica pigments which are sold under the Cab-O-Sil® tradename, and which are commercially available from the Cabot Corporation located in Tuscola, Ill. These colloidal pyrogenic silica pigments are submicroscopic particulated pyrogenic silica pigments having mean particle sizes ranging from about 0.1 microns to about 100 microns. Specific examples of commercially available Cab-O-Sil® silica pigments include Cab-O-Sil® TS-720 (a polydimethylsiloxane treated fumed silica), Cab-O-Sil® TS-530 (a trimethyl silanized fumed silica), and Cab-O-Sil® TS-610 (a dimethyldisilanized fumed silica). The fumed silica provides the lotion compositions with desired viscosity or thickening properties, and is typically included at concentrations ranging from about 0.01% to about 15%, preferably from about 0.1% to about 10%, more preferably from about 1% to about 5% by weight of the lotion composition.

The fumed silica can be used alone or in combination with other optional viscosity or thickening agents such as talc, bentonites including treated bentonites, hectorites including treated hectorites, calcium silicates including treated calcium silicates, magnesium silicates, magnesium aluminum silicates, zinc stearates, sorbitol, colloidal silicone dioxides, spermaceti, carnuba wax, beeswax, candelilla wax, paraffin wax, microcrystalline wax, castrol wax, ceresin, esparto, ouricuri, rezowax, polyethylene wax, $C_{12}$-$C_{24}$ fatty acids, polyhydroxy fatty acid esters, polyhydroxy fatty acid amides, polymethacrylate polymers, polymethacrylate and styrene copolymers, and combinations thereof. These other optional viscosity modifying or thickening agents are also included at total concentrations ranging from about 0.01% to about 15% by weight of the lotion composition. A nonlimiting specific example of another suitable viscosity or thickening agent include bentonite sold as Bentone® 38 which is available from the Rheox Incorporation.

It is preferable that the carrier be hydrophobic. Further, it is preferable that the lotion composition of the present invention comprise no surfactant. Therefore, in a preferred embodiment of the present invention the lotion has a level of hydrophobicity at least as great as that of the topsheet, and the hydrophobicity of the lotion is primarily due to the lack of a surfactant component. If, under some condition, there is a need to raise the wettability of the hydrophobic carrier one may optionally add a wetting agent such as polyoxyethylene alkyl ethers, alkyl ethoxylates, alkylethoxylated amines, polyethylene glycol esters, and/or sorbitan fatty acid esters generally having a low degree of ethoxylation and HLB values below about 7. Suitable additives will be miscible with the carrier so as to form a homogenous mixture. Because of possible skin sensitivity of those using the catamenial device of the present invention, these wetting agents should also be relatively mild and non-irritating to the skin. Typically, these wetting agents are nonionic to be not only non-irritating to the skin, but also to avoid other undesirable effects on any underlying tissue laminate structure, e.g., reductions in tensile strength. Suitable wetting agents will typically have HLB values below 10, preferably below 9, more preferably below 8, and even more preferably below 7.

Non-limiting specific examples of a suitable wetting agents includes nonyl phenol or or polyoxyethylene nonyl phenyl ether (20 of ethoxylation; HLB of 5.7), octyl phenol or polyoxyethylene octyl phenyl ether (10 of ethoxylation; HLB of 3.5), stearyl alcohol or polyoxyethylene stearyl ether (20 of ethoxylation; HLB of 4.9), stearyl amine or polyoxyethylene stearyl amine (20 of ethoxylation; HLB of 4.9), polyethylene glycol 200 dilaurate (HLB 5.9), polyethylene glycol 200 distearate (HLB 4.8), sorbitan monostearate ('Span 60' having HLB 4.7), sorbitan tristearate ('Span 65' having HLB 2.1), sorbitan monooleate ('Span 80' having HLB 4.3), sorbitan trioleate ('Span 85' having HLB 1.8), each of which are available form Cell Chemical Company (Inchon, Korea) or Uniqema (New Castle, Del., USA).

The amount of wetting agent required to increase the wettability of the lotion composition to a desired level will depend upon its HLB value and HLB level of the carrier used, and like factors. The lotion composition can comprise from about 1 to about 50% of the wetting agent when needed to increase the wettability properties of the composition. Preferably, the lotion composition comprises from about 1 to about 25%, most preferably from about 10 to about 20%, of the wetting agent when needed to increase wettability.

Apertured film materials suitable for use as the topsheet include those apertured plastic films that are non-absorbent and pervious to body exudates and provide for minimal or no flow back of fluids through the topsheet. Nonlimiting examples of other suitable formed films, including apertured and non-apertured formed films, are more fully described in U.S. Pat. No. 3,929,135, issued to Thompson on Dec. 30, 1975; U.S. Pat. No. 4,324,246, issued to Mullane et al. on Apr. 13, 1982; U.S. Pat. No. 4,324,314, issued to Radel et al. on Aug. 3, 1982; U.S. Pat. No. 4,463,045, issued to Ahr et al. on Jul. 31, 1984; U.S. Pat. No. 5,006,394, issued to Baird on Apr. 9, 1991; U.S. Pat. No. 4,609,518, issued to Curro et al. on Sep. 2, 1986; and U.S. Pat. No. 4,629,643, issued to Curro et al. on Dec. 16, 1986. Commercially available formed filmed topsheets include those topsheet materials marketed by the Procter & Gamble Company (Cincinnati, Ohio) under the DRI-WEAVE® tradename.

Nonlimiting examples of woven and nonwoven materials suitable for use as the topsheet include fibrous materials made from natural fibers, modified natural fibers, synthetic fibers, or combinations thereof. These fibrous materials can be either hydrophilic or hydrophobic, but it is preferable that the topsheet be hydrophobic or rendered hydrophobic. As an option portions of the topsheet can be rendered hydrophilic, by the use of any known method for making topsheets containing hydrophilic components. One such method include treating an apertured film component of a nonwoven/apertured thermoplastic formed film topsheet with a surfactant as described in U.S. Pat. No. 4,950,264, issued to Osborn on Aug. 21, 1990. Other suitable methods describing a process for treating the topsheet with a surfactant are disclosed in U.S. Pat. Nos. 4,988,344 and 4,988,345, both issued to Reising et al. on Jan. 29, 1991. The topsheet can comprise hydrophilic fibers, hydrophobic fibers, or combinations thereof.

When the topsheet comprises a nonwoven fibrous material in the form of a nonwoven web, the nonwoven web may be produced by any known procedure for making nonwoven webs, nonlimiting examples of which include spunbonding, carding, wet-laid, air-laid, meltblown, needle-punching, mechanical entangling, thermo-mechanical entangling, and hydroentangling. Other suitable nonwoven materials include low basis weight nonwovens, that is, nonwovens having a basis weight of from about 18 $g/m^2$ to about 25 $g/m^2$. An example of such a nonwoven material is commercially available under the tradename P-8 from Veratec, Incorporation, a division of the International Paper Company located in Walpole, Mass.

The backsheet can be any known or otherwise effective backsheet material, provided that the backsheet prevents external leakage of exudates absorbed and contained in the catamenial device. Flexible materials suitable for use as the backsheet include, but are not limited to, woven and non-woven materials, laminated tissue, polymeric films such as thermoplastic films of polyethylene and/or polypropylene, composite materials such as a film-coated nonwoven material, or combinations thereof.

The absorbent core is typically positioned between the topsheet and the backsheet. As used herein, the term "absorbent core" refers to a material or combination of materials suitable for absorbing, distributing, and storing aqueous fluids such as urine, blood, menses, and water found in body exudates. The size and shape of the absorbent core can be altered to meet absorbent capacity requirements, and to provide comfort to the wearer/user. The absorbent core suitable for use in the present invention can be any liquid-absorbent material known in the art for use in absorbent articles, provided that the liquid-absorbent material can be configured or constructed to meet absorbent capacity requirements. Nonlimiting examples of liquid-absorbent materials suitable for use as the absorbent core include comminuted wood pulp which is generally referred to as airfelt; creped cellulose wadding; absorbent gelling materials including superabsorbent polymers such as hydrogel-forming polymeric gelling agents; chemically stiffened, modified, or cross-linked cellulose fibers; meltblown polymers including coform; synthetic fibers including crimped polyester fibers; tissue including tissue wraps and tissue laminates; capillary channel fibers; absorbent foams; absorbent sponges; synthetic staple fibers; peat moss; or any equivalent material; or combinations thereof.

The present invention also relates to methods of treating the skin with the lotion compositions described herein. Generally, a safe and effective amount of the lotion composition is applied to an absorbent article described herein wherein such safe and effective amounts include applying from about 0.0015 $mg/cm^2$ (0.01 $mg/in^2$) to about 100.5 $mg/cm^2$ (100 $mg/in^2$), preferably from about 0.003 $mg/cm^2$ (0.02 $mg/in^2$) to about 12.4 $mg/cm^2$ (80 $mg/in^2$), more preferably from about 0.02 $mg/cm^2$ (0.015 $mg/in^2$) to about 7.75 $mg/cm^2$ (50 $mg/in^2$), of the lotion composition to the absorbent article.

Typically, a safe and effective amount of the lotion compositions of the present invention is applied to an absorbent article such that at least about 0.00015 $mg/cm^2$ (0.001 $mg/in^2$) to about 15.5 $mg/cm^2$ (100 $mg/in^2$), preferably from about 0.0006 $mg/cm^2$ (0.004 $mg/in^2$) to about 11 $mg/cm^2$ (72 $mg/in^2$), more preferably from about 0.005 $mg/cm^2$ (0.03 $mg/in^2$) to about 6.2 $mg/cm^2$ (40 $mg/in^2$), of the composition is transferred to the skin during a single use of an absorbent article which is typically about a three hour period. Absorbent articles are generally changed every three to six hours during the day and once for overnight protection, resulting in at least a safe and effective amount of from about 0.00045 $mg/cm^2$ (0.003 $mg/in^2$) to about 124 $mg/cm^2$ (800 $mg/in^2$), preferably from about 0.0018 $mg/cm^2$ (0.012 $mg/in^2$) to about 88 $mg/cm^2$ (576 $mg/in^2$), more preferably from about 0.015 $mg/cm^2$ (0.09 $mg/in^2$) to about 49.6 $mg/cm^2$ (320 $mg/in^2$), of the lotion composition being administered within a one day interval (24 hour period). However, the transfer of the lotion compositions of the present invention onto a wearer's skin via an absorbent article described herein can occur for one day, several days, weeks, months, or years at appropriate intervals provided that safe and effective amounts of the lotion compositions are administered to deliver the skin treatment benefits described herein.

The lotion compositions of the present invention can be applied to the absorbent articles by any known or otherwise effective technique for distributing a lotion composition onto an absorbent product such as a disposable absorbent article. Nonlimiting examples of methods of applying the lotion compositions onto an absorbent article include spraying, printing (e.g., flexographic printing), coating (e.g., contact slot coating and gravure coating), extrusion, or combinations of these application techniques. The application of the lotion compositions onto an absorbent article facilitates the transfer or migration of the lotion compositions onto the skin for administration and/or deposition of the lotion compositions, resulting in a safe and effective amount of the compositions being applied for improved prevention and reduction of skin disorders. Therefore, the safe and effective amount of the lotion composition that will transfer or migrate to the skin will depend on factors such as the type of lotion composition that is applied, the portion of the body contacting surface where the lotion composition is applied, and the type of absorbent article used to administer the lotion composition.

Any suitable method can be used in determining the amount of a lotion composition described herein that is transferred to the skin of a wearer during use of an absorbent article containing the composition. An example of specific methods for the calculation of transfer amounts of lotion compositions include Gas Chromatographic and other quantitative analytical procedures that involve the analysis of in vivo skin analog materials. A suitable Gas Chromatographic procedure is more fully described in WO 99/45973, Donald C. Roe et al, published Sep. 16, 1999.

The lotion compositions of the present invention may be prepared by any known or otherwise effective technique, suitable for providing a lotion composition comprising the essential skin treatment agents defined herein. In general, the lotion compositions are prepared by first making a carrier system comprising suitable carriers such as petrolatum and behenyl alcohol in combination with a fumed silica thickening agent. Next, a mixture comprising the skin treatment agents and any optional ingredients such as optional skin conditioning agents are added to the carrier system at a melt mix temperature of about 80° C. Although the carrier system, skin treatment agents, and any optional ingredients are typically processed at a temperature of about 80° C., these materials can be processed at temperatures ranging from about 60° C. to about 90° C., preferably from about 70° C. to about 90° C. The resultant lotion composition is subsequently applied to a topsheet component of an absorbent article using a contact applicator such as a Nordsen EP 11-12-02.

The lotion compositions of the present invention are prepared such that the compositions can be applied to an absorbent article to result in safe and effective amounts of the compositions being transferred onto the skin of a wearer of the absorbent article. Therefore, the lotion compositions preferably have a product consistency such that they are relatively immobile and localized on the wearer-contacting surface of the absorbent article at ambient conditions, are readily transferable to the wearer at body temperature, and yet are not completely liquid under extreme storage conditions. In other words, the lotion compositions are solids or semisolids at ambient conditions (about 25° C.) and/or body temperature (about 37° C.) so that the compositions are easily transferred onto the skin by way of normal contact, wearer motion, and/or body heat. The consistency of the lotion compositions can be measured according to ASTM D5 test method which involves the use of a penetrometer to measure consistency. Typically, the lotion compositions of the present invention have a consistency of from about 10 to about 300, preferably from about 20 to about 250, more preferably from about 30 to about 200, as measured at 40° C. according to the test procedure outlined in ASTM D5 test method.

The solid or semisolid consistency of the lotion compositions provide for relatively low levels of the compositions to be applied to the absorbent articles to impart the desired lotion benefits. By "semisolid" is meant that the compositions have a rheology typical of pseudoplastic or plastic liquids such that the compositions remain relatively stationary in a desired location on the absorbent article, and do not have a tendency to flow or migrate to undesired locations of the article. The solid lotion compositions of the present invention likewise can remain in a particular location and not flow or migrate to undesired locations of the article. These solid and semisolid lotion compositions have viscosities high enough to keep the compositions localized on an intended location of the article, but not so high as to impede transfer to the wearer's skin. Typically, final products of solid and semisolid lotion compositions have viscosities ranging from about $1.0 \times 10^6$ centipoise to about $1.0 \times 10^{10}$ centipoise under shear stress conditions of about $3 \times 10^3$ dynes/cm$^2$ at 40° C. (the shear stress applied to the compositions while the absorbent article is in storage or transported at temperature conditions of about 40° C.).

However, the solid and semisolid lotion compositions can be made flowable for transfer or migration of the compositions onto the skin by applying shear stress that results in deformation of the compositions. The shear stress applied at least once during wear of the absorbent article under temperature conditions of about 40° C. is typically at about $1.0 \times 10^6$ dynes/cm$^2$, and this shear stress can result in the lotion compositions having a viscosity of from about $1.0 \times 10^1$ centipoise to about $1.0 \times 10^5$ centipoise. It is believed that the lotion compositions achieve the lower viscosity values under applied shear stress due to the fact that, while the compositions contain solid components, they also contain liquid materials. During wear of an absorbent article described herein, it is desirable to achieve a low viscosity for obtaining sufficient lubrication between the wearer's skin and the body contacting surface of the article to result in effective transfer of the lotion composition onto the wearer's skin. Viscosity at various shear stress can be measured using rheometers known in the art such as the Rheometer SR-2000 available from Rheometrics Incorporation.

The lotion compositions are typically applied to the topsheet of an absorbent article for delivery of the lotion composition onto an external or internal surface of the skin. The lotion composition can be applied to other areas of the absorbent article wherein these areas include wings, side panels, the absorbent core, any secondary layer intermediate the core and topsheet, or any other region of the absorbent article.

Processes for assembling absorbent articles such as the disposable absorbent articles described herein include conventional techniques known in the art for constructing and configuring disposable absorbent articles. For example, the backsheet and/or the topsheet can be joined to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031.

The lotion compositions of the present invention can also be delivered onto the skin by incorporating the compositions into aerosol dispensers, trigger spray dispensers, pump spray dispensers, jars, stick dispensers, cotton balls, patches, sponges, and any other type of known or otherwise effective delivery vehicle.

For catamenial devices the amount of lotion add on level can be significantly higher that that used in other absorbent articles, such as diapers. For example, while not being bound by theory, it is believed that lotion can be added on at levels of 3 mg/cm$^2$, 4 mg/cm$^2$, 5 mg/cm$^2$, 6 mg/cm$^2$, 7 mg/cm$^2$, 8 mg/cm$^2$, 9 mg/cm$^2$, or 10 mg/cm$^2$. These levels refer to the area actually covered by lotion.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A catamenial device having a front end and a back end, said device comprising:
   (a) a topsheet having a body facing surface;
   (b) a backsheet joined to said topsheet; and
   (c) an absorbent core disposed between said topsheet and said backsheet; wherein said absorbent core has a perimeter, a longitudinal centerline, and a transverse centerline;
   wherein said catamenial device further comprises a visible pattern comprising at least one circle and at least two or more slots that are visible when viewing the topsheet;
   wherein said visible pattern comprising at least one circle and at least two or more slots share an imaginary line connecting an edge of one or more slots with an edge of one or more circles;
   wherein the two or more slots are parallel to each other;
   wherein the imaginary line connecting an edge of one or more slots with an edge of one or more circles forms a portion of a perimeter of the visible pattern;
   wherein the slots are cut from the absorbent core; and wherein the slots are distinct and run substantially perpendicular to the longitudinal centerline.

2. The catamenial device of claim 1, wherein the visible pattern comprises three or more slots between the perimeter and the transverse centerline.

3. The catamenial device of claim 1, wherein the visible pattern is tapered towards the front end.

4. The catamenial device of claim 1, wherein the at least one slot communicates flexibility.

5. The catamenial device of claim 1, wherein the circles are located in a loading zone.

6. The catamenial device of claim 1, wherein the back end of the catamenial device can form an inverted V.

7. The catamenial device of claim 1, wherein the visual pattern circles are located in front of at least one slot.

8. The catamenial device of claim 1, wherein said absorbent core comprises a foam.

9. The catamenial device of claim 1, wherein the absorbent core comprises of a first zone, a second zone, and a third zone, and wherein at least two of said absorbent core first zone, second zone, and third zone differ in stiffness.

10. The catamenial device of claim 1, wherein said topsheet further comprises a lotion applied thereto.

11. The catamenial device of claim 1, wherein said absorbent core tapers towards the front end of the catamenial device.

12. A catamenial device having a front end and a back end, said device comprising:
   (a) a topsheet having a body facing surface;
   (b) a backsheet joined to said topsheet; and
   (c) an absorbent core disposed between said topsheet and said backsheet; wherein said absorbent core has a perimeter, a longitudinal centerline, and a transverse centerline;
   wherein said catamenial device further comprises a visible pattern of circles and slots within the absorbent core perimeter;
   wherein the visible pattern is visible when viewing the topsheet;
   wherein said visible pattern of circles and slots share an imaginary straight line connecting an edge of the slots with an edge of a plurality of circles;
   wherein the slots are parallel to each other;
   wherein the imaginary line connecting an edge of the slots with an edge of one or more circles forms a portion of a perimeter of the visible pattern;
   wherein the slots are cut from the absorbent core; and wherein the slots are distinct and run substantially perpendicular to the longitudinal centerline.

13. The catamenial device of claim 12, wherein said absorbent core tapers towards the front end of the catamenial device.

14. The catamenial device of claim 12, wherein the visible pattern comprises three or more slots between the perimeter and the transverse centerline.

15. The catamenial device of claim 12, wherein the visible pattern is tapered towards the front end.

16. The catamenial device of claim 12, wherein the slots communicate flexibility.

17. The catamenial device of claim 12, wherein the back end of the catamenial device can form an inverted V.

18. The catamenial device of claim 12, wherein the visual pattern circles are located in front of at least one slot.

19. The catamenial device of claim 12, wherein said absorbent core tapers towards the front end of the catamenial device.

20. A catamenial device, said device comprising:
   (a) a topsheet having a body facing surface;
   (b) a backsheet joined to said topsheet; and
   (c) an absorbent core disposed between said topsheet and said backsheet; wherein said absorbent core has a perimeter, a longitudinal centerline, and a transverse centerline;
   wherein said catamenial device further comprises a visible pattern comprising one or more circles and one or more slots within the absorbent core perimeter;
   wherein the one or more slots and one or more circles share an imaginary straight line connecting an edge of the one or more slots with an edge of one or more circles;
   wherein the visible pattern and the absorbent core converge towards the longitudinal centerline;
   wherein the imaginary line connecting an edge of the one or more slots with an edge of one or more circles forms a portion of a perimeter of the visible pattern;
   wherein the one or more slots are cut from the absorbent core; and wherein the slots are distinct and run substantially perpendicular to the longitudinal centerline.

* * * * *